(12) United States Patent
Lahr

(10) Patent No.: US 9,678,049 B2
(45) Date of Patent: Jun. 13, 2017

(54) METHOD FOR PROCESSING MEASURED VALUES FROM A NITROGEN OXIDE SENSOR

(71) Applicant: Daimler AG, Stuttgart (DE)

(72) Inventor: Jochen Lahr, Stuttgart (DE)

(73) Assignee: Daimler AG, Stuttgart (DE)

( * ) Notice: Subject to any disclaimer, the term of this patent is extended or adjusted under 35 U.S.C. 154(b) by 84 days.

(21) Appl. No.: 14/433,523

(22) PCT Filed: Sep. 28, 2013

(86) PCT No.: PCT/EP2013/002925
§ 371 (c)(1),
(2) Date: Apr. 3, 2015

(87) PCT Pub. No.: WO2014/053229
PCT Pub. Date: Apr. 10, 2014

(65) Prior Publication Data
US 2015/0276694 A1 Oct. 1, 2015

(30) Foreign Application Priority Data
Oct. 6, 2012 (DE) .................. 10 2012 019 633

(51) Int. Cl.
G01N 33/00 (2006.01)
F01N 3/20 (2006.01)
F01N 9/00 (2006.01)
F02D 41/14 (2006.01)
F01N 3/023 (2006.01)
F02D 41/02 (2006.01)
F02D 41/22 (2006.01)
F02D 41/24 (2006.01)

(52) U.S. Cl.
CPC ......... *G01N 33/0006* (2013.01); *F01N 3/023* (2013.01); *F01N 3/208* (2013.01);
(Continued)

(58) Field of Classification Search
CPC .......... G01N 33/0006; G01N 33/0037; G01N 33/007
See application file for complete search history.

(56) References Cited

U.S. PATENT DOCUMENTS 6,044,689 A * 4/2000 Yoshida ................. G01N 27/12
422/93
2009/0158813 A1 6/2009 Bartley
(Continued)

FOREIGN PATENT DOCUMENTS

DE 100 49 685 A1 4/2002
DE 103 09 422 A1 9/2004
(Continued)

OTHER PUBLICATIONS

International Search Report dated Dec. 2, 2013 with English translation (seven (7) pages).
(Continued)

*Primary Examiner* — Hezron E Williams
*Assistant Examiner* — David Z Huang
(74) *Attorney, Agent, or Firm* — Crowell & Moring LLP

(57) ABSTRACT

A method for processing measured values two nitrogen oxide sensors, one of which is arranged upstream of a nitrogen oxide reduction catalytic converter in the exhaust gas system of a motor vehicle and the other of which is arranged downstream of the nitrogen oxide reduction catalytic converter, involves recording and comparing measured values from the two nitrogen oxide sensors at least approximately at the same time. A sensitivity of the first nitrogen oxide sensor and/or of the second nitrogen oxide sensor is changed depending on the result of the comparison.

13 Claims, 1 Drawing Sheet

(52) U.S. Cl.
CPC ............. *F01N 9/00* (2013.01); *F02D 41/029* (2013.01); *F02D 41/146* (2013.01); *F02D 41/2474* (2013.01); *G01N 33/007* (2013.01); *G01N 33/0037* (2013.01); *F01N 2560/026* (2013.01); *F01N 2560/14* (2013.01); *F01N 2900/0416* (2013.01); *F02D 41/1441* (2013.01); *F02D 41/222* (2013.01); *F02D 41/2441* (2013.01); *Y02T 10/24* (2013.01); *Y02T 10/47* (2013.01)

(56) References Cited

U.S. PATENT DOCUMENTS

| | | |
|---|---|---|
| 2010/0257846 A1 | 10/2010 | Weber |
| 2010/0293925 A1 | 11/2010 | Lahr et al. |
| 2010/0326165 A1* | 12/2010 | Rauworth .......... G01N 33/0006 73/1.06 |
| 2011/0252767 A1 | 10/2011 | Lin et al. |
| 2012/0233984 A1* | 9/2012 | Levijoki ................ F01N 3/035 60/274 |

FOREIGN PATENT DOCUMENTS

| | | |
|---|---|---|
| DE | 10 2004 051 747 A1 | 4/2006 |
| DE | 10 2008 005 640 A1 | 7/2009 |

OTHER PUBLICATIONS

German-language Written Opinion (PCT/ISA/237) dated Dec. 2, 2013 (five (5) pages).
German Search Report dated May 14, 2013, including partial English translation (ten (10) pages).

\* cited by examiner

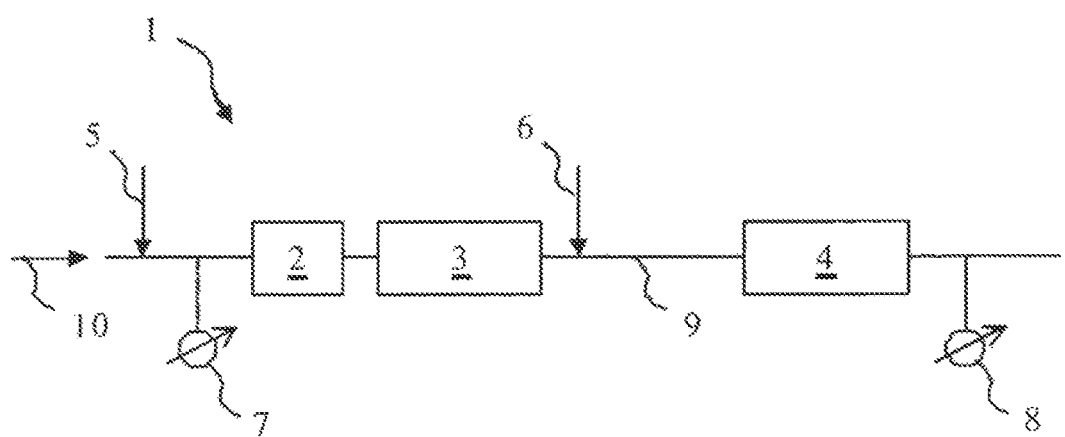

METHOD FOR PROCESSING MEASURED VALUES FROM A NITROGEN OXIDE SENSOR

BACKGROUND AND SUMMARY OF THE INVENTION

Exemplary embodiments of the invention relate to a method for processing measured values from a nitrogen oxide sensor.

German patent document DE 10 2008 005 640 A1 discloses a method for determining a nitrogen dioxide concentration in an exhaust gas system of an internal combustion engine in which the output signals of two nitrogen oxide sensors are compared with one another. Here, the first nitrogen oxide sensor is arranged before and the second nitrogen oxide sensor after an exhaust gas treatment element with the capability of being able to convert nitrogen monoxide (NO) to nitrogen dioxide ($NO_2$). This allows compensation for a different operating sensitivity with respect to NO and $NO_2$, which is present with conventional nitrogen oxide sensors.

Exemplary embodiments of the invention are directed to a method that allows an accurate determination of a nitrogen oxide content in exhaust gas of an internal combustion engine.

With the method according to the invention, measured values from a first and a second nitrogen oxide sensor are processed. The first nitrogen oxide sensor is arranged upstream of a nitrogen oxide reduction catalytic converter in the exhaust gas system of a motor vehicle and the second nitrogen oxide sensor is arranged downstream of the nitrogen oxide reduction catalytic converter. With the method, measured values from the first and second nitrogen oxide sensors are recorded and compared with one another at least approximately at the same time, wherein the sensitivity of the first nitrogen oxide sensor and/or of the second nitrogen oxide sensor is changed depending on the result of the comparison. This allows compensation for undesirable sensitivity tolerances of the nitrogen oxide sensors, typically caused by production spread. The nitrogen oxide sensors are preferably such of the same design.

The sensitivity of the first and/or of the second nitrogen oxide sensor can, for example, be changed by changing the gain. Here, the change can occur directly at the output signal of the sensor; however, it can also occur as a result of signal correction at a control device to which the sensor or sensors are connected and which processes the signals of the sensor or sensors.

In an embodiment of the invention, the sensitivity of the first nitrogen oxide sensor and/or of the second nitrogen oxide sensor is changed in such a way that the first nitrogen oxide sensor and the second nitrogen oxide sensor have at least approximately the same sensitivity with respect to NO and/or $NO_2$. Typically, the sensors provide an output signal that correlates with the sum of NO and $NO_2$, i.e., with the concentration of nitrogen oxides (NOx), in the exhaust gas. The output signal is therefore an NOx concentration or content signal. The comparison of the measured values from the first and from the second nitrogen oxide sensor is preferably carried out under conditions with which the same concentrations or contents of NOx in the exhaust gas can be expected at the location of the sensors. When changing the sensitivity depending on the signal comparison, the signal from the sensor that indicates a lower NOx concentration, for example, can be increased to the signal of the sensor with the higher indication. Conversely, the signal from the NOx sensor with the higher measured value is reduced accordingly. However, the signals from the two sensors can adjusted to a mean value. In the cases mentioned, after carrying out the signal comparison and the sensitivity change, the nitrogen oxide sensors have at least approximately the same signals or the signals are corrected to an at least approximately equal value.

To avoid the influence of any cross-sensitivity of the nitrogen oxide sensors that may be present, in a further embodiment of the invention, the comparison is carried out at a time at which at least approximately equal concentrations of hydrocarbons (HC) and/or NOx are present in the exhaust gas at the point where the first nitrogen oxide sensor is installed and at the point where the second nitrogen oxide sensor is installed.

In a further advantageous embodiment of the invention, the comparison is carried out at a time at which the concentrations of hydrocarbons and/or ammonia ($NH_3$) in the exhaust gas do not exceed specified limits at the point where the first nitrogen oxide sensor is installed and at the point where the second nitrogen oxide sensor is installed. This enables cross-sensitivity effects of the sensors with regard to HC and $NH_3$ to be particularly effectively excluded. In particular, the limit values are set low. Preferably, the limit values lie below 20 ppm, particularly preferably below 10 ppm or even below 5 ppm.

In a further embodiment of the invention, the comparison is carried out at a time at which the exhaust gas temperature exceeds a specifiable temperature limit at the point where the first nitrogen oxide sensor is installed and at the point where the second nitrogen oxide sensor is installed. The temperature is preferably chosen such that the thermodynamic NO—$NO_2$ balance lies predominantly on the side of NO. This is the case at temperatures above approximately 350° C. The comparison is therefore preferably carried out at a temperature limit of 400° C., in particular of 450° C. and particularly preferably at a temperature limit of 500° C. for the exhaust gas temperature. If a particulate filter is fitted in the exhaust gas system in question, then these conditions are usually fulfilled when a thermal regeneration of the particulate filter is carried out by burning off carbon black with oxygen. In a further advantageous embodiment of the invention, the comparison therefore takes place immediately following such a thermal particulate filter regeneration.

Advantageous embodiments of the invention are illustrated in the drawings and are described below. In doing so, the characteristics stated above and still to be described below can be used not only in the specified combination of characteristics in each case, but also in other combinations or in their own right without departing from the scope of the present invention.

BRIEF DESCRIPTION OF THE DRAWING FIGURE

The single FIGURE shows a schematic block diagram of an exhaust gas treatment system connected to a motor vehicle internal combustion engine.

DETAILED DESCRIPTION

In the FIGURE, an exhaust gas treatment system 1 of a motor vehicle internal combustion engine, in particular of a diesel engine, is shown only roughly schematically. Exhaust gas of the internal combustion engine (not shown) accordingly enters the exhaust gas treatment system 1 in the direction indicated by the arrow 10. Viewed in the direction of exhaust gas flow, this successively incorporates an oxidation catalytic converter 2, a particulate filter 3 and an SCR catalytic converter 4 in an exhaust gas pipe 9. The SCR catalytic converter 4 can also be designed as a two-way catalytic converter arrangement of two catalytic converter units connected in parallel.

The exhaust gas treatment device 1 further incorporates a fuel feed device 5 upstream of the oxidation catalytic converter 2. A hydrocarbon and/or hydrogen-containing fuel can be introduced into the exhaust gas system 9 via the fuel feed device 5. Preferably, the fuel feed device 5 is designed to feed a fuel that is present on board the vehicle, in particular provided for the driving thereof, to the exhaust gas.

A reducing agent incorporating $NH_3$ in free or bonded form for selective catalytic NOx reduction can be fed to the exhaust gas by means of a reducing agent feed device 6. Without restricting generality, it is assumed below that the reducing agent is an aqueous urea solution (HWL). The HWL preferably has a target urea concentration of approximately 32% and is taken from a storage container (not shown).

Furthermore, a first sensor 7 that is sensitive to NOx is provided upstream of the SCR catalytic converter 4. As shown, this is arranged between the fuel feed device 5 and the oxidation catalytic converter 2 in the exhaust pipe 9. An arrangement at a different point upstream of the SCR catalytic converter 4, for example between the particulate filter 3 and the reducing agent feed device 6, can likewise be provided. A further, second NOx sensor 8 is arranged downstream of the SCR catalytic converter 4 in the exhaust gas pipe 9. Here, the NOx sensors are preferably of the same design. Preferably, the NOx turnover of the SCR catalytic converter 4 is determined by evaluating the signals output by the NOx sensors 7, 8, and an HWL feed quantity for reducing nitrogen oxide is set accordingly at the SCR catalytic converter. A control device (not shown), which receives and is able to process the signals from the NOx sensors 7, 8, is preferably provided for this purpose. Preferably, this control device can also control the operation of the feed devices 5, 6 and carry out further control and evaluation functions relating to the operation of the internal combustion engine and to the exhaust gas treatment system 1.

It is understood that the exhaust gas treatment system 1 can also incorporate further catalytic or filtering components for cleaning the exhaust gas that are not shown separately here. In particular, a nitrogen oxide storage catalytic converter can be provided upstream of the oxidation catalytic converter and/or between the oxidation catalytic converter 2 and the particulate filter 3 and/or between the particulate filter 3 and the SCR catalytic converter 4. Particularly preferably, an ammonia trap catalytic converter for oxidizing $NH_3$ slip is provided after the SCR catalytic converter 4. Preferably, additional exhaust gas, pressure and temperature sensors (not shown), the signals of which enable the operation of the exhaust gas treatment system 1 and the internal combustion engine to be adjusted as required, are also provided. Temperature sensors are preferably provided in each case before and after the oxidation catalytic converter 2 and/or the particulate filter 3 and/or the SCR catalytic converter 4.

The oxidation catalytic converter 2 is preferably designed as a so-called diesel oxidation catalytic converter having a coating with low or non-existent oxygen storage capability. A coating with a three-way catalytic converter function can also be provided. A carrier for the coating is preferably in the form of a ceramic carrier or metal foil carrier body. A heating element, preferably in the form of a coated metal foil carrier body (so-called E-Cat) can also be provided immediately upstream.

The particulate filter 3 can be constructed in sinter metal design or as a filter unit with a honeycomb body design with flow through the walls. Preferably, a catalytic coating, for example with an oxidation-catalytically active material and/or with an SCR catalytic converter material, is provided for the particulate filter 3. Under oxidizing conditions, the SCR catalytic converter material is able to catalyze a selective, continuous reduction of NOx by means of stored and/or fed-in ammonia ($NH_3$) as a selective NOx reducing agent. A zeolith containing iron or copper is preferred as the catalytic converter material. At the same time, the SCR catalytic converter material can be provided on the raw gas side and/or on the clean gas side of the filtering surfaces of the particulate filter 3. In the preferred embodiment of the particulate filter 3 as a conventional filter with a honeycomb body design with flow through the walls, any coating with the appropriate SCR catalytic converter material that may be present is preferably provided on the channel walls exposed to the raw gas. Particularly in this case, it can be advantageous to provide the SCR catalytic converter coating only in sections on the inlet side or on the outlet side on channel walls of the particulate filter 3. For example, a coating with the SCR catalytic converter material can be provided over a first part of the axial extension of the particulate filter 3 of approximately 50% of the length. The rear part viewed in the axial direction can be uncoated or provided with an oxidation-catalytically active coating.

The SCR catalytic converter 4 arranged downstream of the particulate filter 3 is provided with the capacity for selective reduction of NOx with $NH_3$ in a similar way to any SCR coating of the particulate filter 3 that may be present and preferably designed in the same way with regard to such a coating. For maximum effectiveness, two different SCR coatings with different temperature range arranged one after the other in the direction of the exhaust gas flow can also be provided on one and the same carrier body or on two carrier bodies arranged one after the other a short distance apart. Zoned coatings comprising an iron and a copper-containing zeolith are preferred. Preferably, the SCR catalytic converter 4 is arranged remotely from the engine in the underfloor region of the vehicle. In any case, an arrangement in the exhaust gas system 9 in such a way that the temperature of the SCR catalytic converter 4 does not exceed 650° C. in the event of a thermal particulate filter regeneration is particularly preferred. Geometric removal from the particulate filter 3 in conjunction with an appropriate sizing of the exhaust gas pipe 9 with regard to heat dissipation enables a temperature gradient of more than 200° C. or more to be achieved between a particulate filter 3 heated to approximately 800° C. and the SCR catalytic converter 4.

In order to carry out a thermal regeneration of the particulate filter 3 by burning off carbon black, the fuel feed device 5 is activated and fuel, in particular diesel fuel, is added to the exhaust gas. By oxidizing the fuel at the oxidation catalytic converter 2, the exhaust gas fed to the particulate filter 3 and the particulate filter 3 are heated to a temperature of approximately 650° C. to 850° C. required for burning off carbon black. A feed of fuel is usually required for the whole duration of the thermal particulate filter regeneration, possibly with interruptions, in order to maintain the temperature of the particulate filter 3 at the required temperature for burning off carbon black.

The signals from the two NOx sensors 7, 8 are evaluated with regard to various functions, such as for example for determining an HWL dosing quantity, an ageing determination of oxidation catalytic converter 2, particulate filter 3 and/or SCR catalytic converter 4, and various other diagnostic functions. For this reason, the reliability and the accuracy of the signals or measured values provided are particularly important. However, the accuracy of the signals relating to a measured value that indicates the NOx concentration in the exhaust gas is typically limited due to tolerances of up to approximately +/−15%. Alongside this, there are usually more or less strong cross-sensitivities, in particular with regard to HC and $NH_3$. In addition, the sensitivities with respect to NO and $NO_2$ are typically different. The way in which a sensor calibration is preferably carried out with regard to the display sensitivity with respect to NOx, particularly taking into account the cross-sensitivities, is explained below.

According to the invention, the sensor calibration is carried out immediately or shortly after a thermal regeneration of the particulate filter 3. Here, the temperature of the particulate filter 3 is increased to a value that is sufficient for burning off carbon black with oxygen. Typically, the particulate filter is heated to 550° C. or more. Measures internal to the engine, such as for example early fuel post-injection, are first undertaken for this purpose. These measures are preferably maintained until the oxidation catalytic converter 2 is able to reliably convert hydrocarbons by oxidation. The fuel feed device 5 is then activated and fuel fed to the exhaust gas. Oxidizing the added fuel at the oxidation catalytic converter 2 leads to a further heating of the particulate filter 3 to a temperature required for burning off carbon black.

The conditions for thermal particulate filter regeneration are preferably maintained until carbon black which has collected in the particulate filter 3 has been extensively removed or removed to a specifiable degree. In this time, a status bit of the control device is set, as a result of which active particulate filter regeneration is indicated. The particulate filter regeneration can last up to 15 minutes or even longer. At the end of the particulate filter regeneration, i.e. after the appropriate status bit has been reset, the preferred conditions for a comparison of the measured values and for any correction of the measured values or signals that may be necessary, or a sensitivity calibration of the NOx sensors 7, 8, are present. The conditions are such that it can be assumed that the first NOx sensor 7 and the second NOx sensor 8 return the same measured values. In detail, the conditions include:

The NOx concentrations in the exhaust gas are at least approximately equal at the point at which the NOx sensors 7, 8 are installed and correspond extensively to the NOx raw emission of the internal combustion engine. In the present case, this is guaranteed as the exhaust gas system is extensively free from constituents that can reduce NOx. More accurately, a feed of fuel containing HC, CO and/or $H_2$ via the fuel feed device 5 is terminated and the internal combustion engine is operated in a lean condition and with at least approximately full fuel combustion. However, as a result, the further condition is also fulfilled that the NOx sensors 7, 8 are subjected to exhaust gas which is extensively free from reducing constituents which, due to cross-sensitivities, could affect the measured values of the NOx sensors 7, 8 or react reductively with NOx. In particular, the HC concentration in the exhaust gas lies below a specifiable limit of 10 ppm or less.

HWL dosing is terminated no later than this point in time. Preferably, it has already been terminated, for example on conclusion of the heating measures internal to the engine for heating the particulate filter 3. As a result of the previous particulate filter regeneration, the SCR catalytic converter 4 has an increased temperature of at least 400° C., which typically has also been present for at least some minutes. It is therefore guaranteed that any $NH_3$ that may have been adsorbed in the SCR catalytic converter 4 is at least approximately fully desorbed and the SCR catalytic converter 4 is therefore extensively free from stored $NH_3$. Due to the comparatively high temperatures of the particulate filter regeneration, any urea deposits that may be present in the exhaust gas system 9 are vaporized. This guarantees that the $NH_3$ concentration in the exhaust gas in the whole exhaust gas system 9, and particularly also at the location of the second NOx sensor 8, is negligible or lies below a limit of preferably 10 ppm or less. All in all, this prevents the signal from the second NOx sensor 8 being affected by $NH_3$ and prevents a turnover of NOx made possible by the SCR catalytic converter 4.

Further, a limiting temperature of at least 400° C., preferably at least 450° C. and particularly preferably of at least 500° C. at the location of the first NOx sensor 7 and/or at the location of the second NOx sensor 8 is exceeded. The $NO_2$ content of the NOx contained in the exhaust gas is therefore comparatively low for thermodynamic reasons and a different sensitivity of the NOx sensors 7, 8 with respect to NO and $NO_2$ which may exist does not impact the respective measuring signal or only impacts it to a small extent.

All in all, it is therefore to be expected that the NOx sensors 7, 8 output signals of the same magnitude or the same measured values are present. Under these conditions, preferably immediately after termination of a thermal particulate filter regeneration or at a specifiable short time later, measured values from the NOx sensors 7, 8 are recorded at least at approximately the same time and subsequently compared with one another. In doing so, it is preferred to average a collective of measured values of a plurality of measured values which are recorded in quick succession.

If the measured values are scattered by more than a specifiable amount of, for example, 15%, then it can be assumed that at least one of the two NOx sensors 7, 8 is faulty. In this case, a fault signal can be output. If the measured values are less widely scattered, a measured value comparison is carried out. In doing so, the measured value from one of the NOx sensors 7, 8 can be corrected in such a way that it corresponds to the measured value from the other NOx sensor, which is left unchanged. It can also be provided that the measured value from the NOx sensor lying closer to an NOx raw emission value calculated for the present engine operating point be specified as a reference value, and the measured value from the other NOx sensor corrected to this value. It is also possible for both measured values to be changed, preferably corrected to the common mean value. In each case, the sensitivities of the NOx sensors 7, 8 with respect to NOx after carrying out the calibration or correction are equal. The correction can be carried out at the sensor itself or in the connected control device which processes and conditions the signals.

The described method according to the invention enables the tolerances of the NOx sensors 7, 8 to be compensated for and, as a result, an improved HWL dosing accuracy and a more reliable monitoring of virtually the whole exhaust gas treatment system 1 to be achieved.

The foregoing disclosure has been set forth merely to illustrate the invention and is not intended to be limiting.

Since modifications of the disclosed embodiments incorporating the spirit and substance of the invention may occur to persons skilled in the art, the invention should be construed to include everything within the scope of the appended claims and equivalents thereof.

The invention claimed is:

1. A method, comprising:
    measuring, by a first nitrogen oxide sensor arranged upstream of a nitrogen oxide reduction catalytic converter in an exhaust gas system of a motor vehicle, a nitrogen oxide content of exhaust gas;
    measuring, by a second nitrogen oxide sensor arranged downstream of the nitrogen oxide reduction catalytic converter, the nitrogen oxide content of the exhaust gas,
    wherein the measurements of the nitrogen oxide content of the exhaust gas by the first and second nitrogen oxide sensors occur at least approximately at a same time and at a time at which conditions exist such that a same measured value of the nitrogen oxide content of the exhaust gas should be measured by both the first and second nitrogen oxide sensors;
    comparing the measurements of the nitrogen oxide content of the exhaust gas by the first and second nitrogen oxide sensors; and
    adjusting a sensitivity of the first nitrogen oxide sensor or of the second nitrogen oxide sensor if the comparison indicates that respective measured values of the nitrogen oxide content of the exhaust gas by the first and second nitrogen oxide sensors differ by more than a specified amount, wherein the sensitivity of the first nitrogen oxide sensor or of the second nitrogen oxide sensor is changed in such a way that the first nitrogen oxide sensor and the second nitrogen oxide sensor have at least approximately equal sensitivities with respect to NO and/or $NO_2$.

2. The method of claim 1, wherein the sensitivity of the first nitrogen oxide sensor or of the second nitrogen oxide sensor is changed in such a way that the sensitivity of the first nitrogen oxide sensor or of the second nitrogen oxide sensor is adapted to the sensitivity of the respective other nitrogen oxide sensor that is left unchanged.

3. The method of claim 1, wherein the sensitivity of the first nitrogen oxide sensor or of the second nitrogen oxide sensor is changed in such a way that the sensitivity of the nitrogen oxide sensor, the measured value from which deviates more strongly from a calculated NOx raw emission value, is adapted to the sensitivity of the other nitrogen oxide sensor.

4. The method of claim 1, wherein the sensitivity of the first nitrogen oxide sensor and of the second nitrogen oxide sensor are changed in such a way that the measured values from the nitrogen oxide sensors correspond to a mean value of the measured values from the nitrogen oxide sensors before carrying out the sensitivity change.

5. The method of claim 1, wherein the measurements are carried out at a time at which at least approximately equal concentrations of hydrocarbons or NOx are present in the exhaust gas at a point where the first nitrogen oxide sensor is installed and at a point where the second nitrogen oxide sensor is installed.

6. The method of claim 5, wherein the measurements are carried out at a time at which the concentrations of hydrocarbons and/or ammonia in the exhaust gas do not exceed specified limits of, in each case, less than 20 ppm at the point where the first nitrogen oxide sensor is installed and at the point where the second nitrogen oxide sensor is installed.

7. The method of claim 5, wherein the measurements are carried out at a time at which a temperature of the exhaust gas exceeds 450° C. at the point where the first nitrogen oxide sensor is installed and at the point where the second nitrogen oxide sensor is installed.

8. The method of claim 1, wherein the measurements are carried out at a time at which concentrations of hydrocarbons and/or ammonia in the exhaust gas do not exceed specified limits of, in each case, less than 6 ppm at a point where the first nitrogen oxide sensor is installed and at a point where the second nitrogen oxide sensor is installed.

9. The method of claim 8, wherein the measurements are carried out at a time at which a temperature of the exhaust gas exceeds 450° C. at the point where the first nitrogen oxide sensor is installed and at the point where the second nitrogen oxide sensor is installed.

10. The method of claim 1, wherein the measurements are carried out at a time at which a temperature of the exhaust gas exceeds 450° C. at a point where the first nitrogen oxide sensor is installed and at a point where the second nitrogen oxide sensor is installed.

11. The method of claim 1, wherein an error signal is output when the measured values from the nitrogen oxide sensors deviate from one another by more than a predefinable amount.

12. The method of claim 1, wherein the measurements take place immediately following a thermal regeneration of a particulate filter arranged in the exhaust gas system.

13. The method of claim 1, wherein an oxidation catalytic converter, a particulate filter and the nitrogen oxide reduction catalytic converter are arranged in the exhaust gas system one after the other in a direction of the exhaust gas flow, and the first nitrogen oxide sensor is arranged on an input side of the oxidation catalytic converter and the second nitrogen oxide sensor is arranged downstream of the nitrogen oxide reduction catalytic converter.

* * * * *